United States Patent [19]

Andree et al.

[11] Patent Number: 5,074,677
[45] Date of Patent: Dec. 24, 1991

[54] CENTER-FREE LARGE ROLLER BEARING

[75] Inventors: Dietrich Andree, Dortmund; Dieter Becker, Lippstadt-Esbeck; Heinrich Siemensmeyer, Dortmund; Johannes Wozniak, Lippstadt, all of Fed. Rep. of Germany

[73] Assignee: Hoesch AG, Dortmund, Fed. Rep. of Germany

[21] Appl. No.: 568,404

[22] Filed: Aug. 16, 1990

[30] Foreign Application Priority Data

Aug. 17, 1989 [DE] Fed. Rep. of Germany ....... 3927077

[51] Int. Cl.⁵ .............................................. F16C 19/52
[52] U.S. Cl. ..................................... 384/448; 384/622
[58] Field of Search ............... 384/448, 455, 619, 622, 384/452

[56] References Cited

U.S. PATENT DOCUMENTS

| 3,652,141 | 3/1972 | Hüsten et al. | 384/455 |
| 4,798,299 | 1/1989 | Bayer et al. | 384/448 |
| 4,828,405 | 5/1989 | Sinner | 384/455 |
| 4,865,468 | 9/1989 | Kato et al. | 384/448 |
| 4,989,999 | 2/1991 | Siemensmeyer | 384/455 |

Primary Examiner—Lenard A. Footland
Attorney, Agent, or Firm—Max Fogiel

[57] ABSTRACT

A large open-center roller bearing consisting of single or multiple outer and inner rings with rollers rolling over races between the rings, wherein one ring can accommodate an ultrasonic probe and the other ring has a contact surface. The object is to provide a bearing that can be simply and reliably tested by ultrasound. One or more contact surfaces (19, 24, and 25) extend around one or more of the outer surfaces of the ring (2 or 3) being tested.

8 Claims, 1 Drawing Sheet

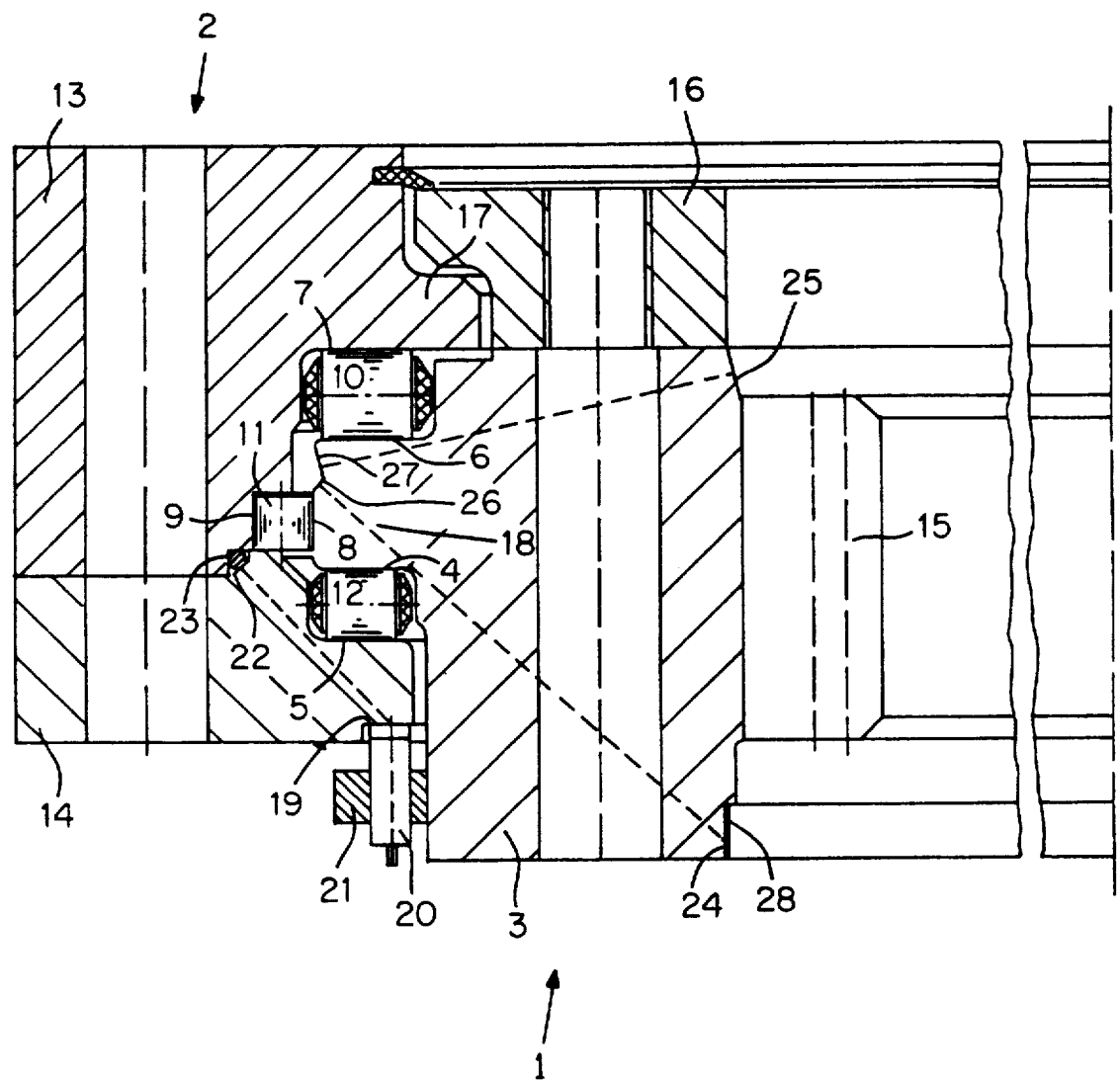

1

CENTER-FREE LARGE ROLLER BEARING

BACKGROUND OF THE INVENTION

In various applications involving large roller bearings it makes sense to have available an ultrasonic testing device that allows non-destructive detection of defects in the material with no need to dismantle the bearing. This is especially true of the large roller bearings employed as rotary joints in offshore cranes.

European Patent A 1 228 731 proposes providing at least one opening in at least one ring to accommodate an ultrasonic probe. Material defects in the other ring are then detected by way of a contact surface in that ring. One drawback of this system is that the ultrasonic probe must be positioned in the vicinity of the races. At least some of the lubricant must accordingly be removed from that vicinity and the contact surface must at least to some extent be cleaned. Furthermore, any worn-off particles that accumulate in the area can contaminate the results. Again, once the bearing has been used for a while, the permissible wear will increase play. The increased play will shift the contact surface in relation to the ultrasonic probe, which can also lead to errors in measurement.

SUMMARY OF THE INVENTION

The object of the present invention is to eliminate the aforesaid drawbacks and provide a bearing that can be simply and reliably tested by ultrasound.

The large roller bearing in accordance with the invention facilitates the positioning of an ultrasonic probe in a practical way. It is no longer necessary to apply it to inaccessible points because the areas where the probe contacts the bearing are distributed around the outer surface of the ring being tested. Furthermore, no special preparations are necessary prior to testing. All that is necessary is to remove the anticorrosion coating, the jacketing ring, or a jacketing strip from the contact surface. Any play that has developed in the bearing and any worn-off particles that have accumulated in the vicinity of the races will have no effect on the precision of the measurement. Again, the surface in a projection from the contact surface to the testing field provides a surrounding reference surface perpendicular to the contact surface. This measure ensures an unexceptionable rear-wall echo and hence precise identification of the location of any defect.

BRIEF DESCRIPTION OF THE DRAWINGS

One embodiment of the invention will now be described in detail with reference to the drawing, which is a section through half of a large open-center roller bearing.

DESCRIPTION OF THE PREFERRED EMBODIMENTS

A large roller bearing 1 consists of an outer ring 2 and an inner ring 3, between which rollers 10, 11, and 12 roll over races 4, 5, 6, 7, 8, and 9. The present embodiment of a bearing is a three-row rotary joint with its outer ring 2 comprising two subsidiary rings 13 and 14.

Inner ring 3 is rotated by teeth 15. To prevent catastrophes inner ring 3 has a holder 16 that engages the outside of a collar 17 on subsidiary ring 13. Inner ring 3 has a nose 18, around which all three inner-ring races 4, 6, and 8 extend. Between nose 18 and outer ring 2 are supporting rollers 10, radial rollers 11, and retaining rollers 12.

In this embodiment the transition to retaining-roller race 5 in the subsidiary ring 14 of outer ring 2 is considered to be an area that is likely to crack. Other areas considered likely to crack in inner ring 3 are the transitions to retaining-roller race 4 and to supporting-roller race 6. A contact surface 19 is accordingly positioned on the outer surface of outer ring 2 for an ultrasonic probe 20 to be applied to. The probe is held against inner ring 3 by a holder 21. The holder can be for example a magnetic base. Ultrasonic probe 20 emits testing pulses at an angle to ensure that the area at risk at the transition to retaining-roller race 5 will be optimally covered. In a projection of the direction of sound is a reference surface 22, which is used to verify and calibrate the ultrasonic measurements. The embodiment described herein employs for a reference surface 22 a surface that is already present for the purpose of accommodating a seal 23. Two additional contact surfaces 24 and 25 are provided on inner ring 3. As will be evident from the drawing, it is also conceivable for ultrasonic probe 20 to emit pulses at any desired angle to contact surfaces 25 and 24 as well as at a right angle to contact surface 25. Contact surface 24 has a jacketing strip 28 over it. The reference surfaces 26 and 27 in the illustrated embodiment are at the outside diameter of the nose adjacent to the radial-roller race 8.

We claim:

1. A large open-center roller bearing comprising: at least one outer ring and one inner ring; rollers rolling over races between said rings; an ultrasonic probe on one of said rings; the other ring having at least one contact surface on at least one outer surface of said other ring to be tested by said ultrasonic probe; said ultrasonic probe being secured to the outer surface free of a recess on said one ring; said ultrasonic probe having a test field, a projection of the direction of sound from said contact surface forming a surrounding reference surface to said test field and perpendicular to said test field.

2. A large open-center roller bearing comprising: at least one outer ring and one inner ring; rollers rolling over races between said rings; an ultrasonic probe on one of said rings; the other ring having at least one contact surface on at least one outer surface of said other ring to be tested by said ultrasonic probe; said ultrasonic probe being secured to the outer surface free of a recess on said one ring; said contact surface being distributed around said outer surface of said other ring to be tested, said ultrasonic probe having a measurement precision independent of play in said bearing and independent of worn-off particles accumulated adjacent said races, a surface in a projection from said contact surface providing a surrounding reference surface perpendicular to said contact surface with a rear-wall echo for locating precisely any defect.

3. A large open-center roller bearing comprising: at least one outer ring and one inner ring; rollers rolling over races between said rings; an ultrasonic probe on one of said rings; the other ring having at least one contact surface on at least one outer surface of said other ring to be tested by said ultrasonic probe; said ultrasonic probe being secured to the outer surface free of a recess on said one ring.

4. A large open-center roller bearing as defined in claim 3, wherein said contact surface has an anticorrosion coating.

5. A large open-center roller bearing as defined in claim 3, wherein said contact surface has a jacketing ring-shaped element.

6. A large open-center roller bearing as defined in claim 3, wherein said contact surface has a jacketing strip.

7. A large open-center roller bearing as defined in claim 3, including a holder for holding said ultrasonic probe and secured adjacent to an outer surface of said one ring.

8. A large open-center roller bearing as defined in claim 3, wherein said contact surface has an anticorrosion coating; said contact surface being distributed around said outer surface of said other ring to be tested, said ultrasonic probe having a measurement precision independent of play in said bearing and independent of worn-off particles accumulated adjacent said races, a surface in a projection from said contact surface providing a surrounding reference surface perpendicular to said contact surface with a rear-wall echo for locating precisely any defect; said contact surface having a jacketing ring-shaped element; and a holder for holding said ultrasonic probe secured adjacent to one outer surface of said one ring.

* * * * *